United States Patent
Hoey et al.

(10) Patent No.: US 10,806,502 B2
(45) Date of Patent: *Oct. 20, 2020

(54) SYSTEMS AND METHODS FOR TREATING THE PROSTATE

(71) Applicant: Boston Scientific Scimed, Inc., Maple Grove, MN (US)

(72) Inventors: Michael Hoey, Shoreview, MN (US); Roger Noel Hastings, Naples, FL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/980,295

(22) Filed: May 15, 2018

(65) Prior Publication Data

US 2018/0256238 A1    Sep. 13, 2018

Related U.S. Application Data

(63) Continuation of application No. 14/566,448, filed on Dec. 10, 2014, now Pat. No. 9,968,395.

(Continued)

(51) Int. Cl.
*A61B 18/04* (2006.01)
*A61B 34/20* (2016.01)
(Continued)

(52) U.S. Cl.
CPC .............. *A61B 18/04* (2013.01); *A61B 34/20* (2016.02); *A61B 1/00154* (2013.01); *A61B 1/05* (2013.01);
(Continued)

(58) Field of Classification Search
CPC  A61B 2018/00029; A61B 2018/00547; A61B 2018/00577; A61B 2018/00904;
(Continued)

(56) References Cited

U.S. PATENT DOCUMENTS

| 408,899 A | 8/1889 | Small |
|---|---|---|
| 1,719,750 A | 7/1929 | Bridge et al. |

(Continued)

FOREIGN PATENT DOCUMENTS

| CN | 2061443 U | 9/1990 |
|---|---|---|
| CN | 2418844 Y | 2/2001 |

(Continued)

OTHER PUBLICATIONS

US 5,326,343 A, 07/1994, Rudie et al. (withdrawn)

(Continued)

*Primary Examiner* — Aaron B Fairchild
(74) *Attorney, Agent, or Firm* — Bookoff McAndrews, PLLC

(57) ABSTRACT

A vapor delivery system and method is provided that is adapted for treating prostate tissue. The vapor delivery system includes a vapor delivery needle configured to deliver condensable vapor energy to tissue. In one method, the vapor delivery system is advanced transurethrally into the patient to access the prostate tissue. The vapor delivery system is properly positioned by measuring and advancing the system based on a field-of-view of an endoscope or camera disposed within the system.

7 Claims, 6 Drawing Sheets

Related U.S. Application Data

(60) Provisional application No. 61/914,279, filed on Dec. 10, 2013.

(51) Int. Cl.
    *A61B 1/307* (2006.01)
    *A61B 1/05* (2006.01)
    *A61B 18/00* (2006.01)
    *A61B 17/00* (2006.01)
    *A61B 1/00* (2006.01)

(52) U.S. Cl.
    CPC ......... *A61B 1/307* (2013.01); *A61B 17/00234* (2013.01); *A61B 2017/00274* (2013.01); *A61B 2018/00029* (2013.01); *A61B 2018/00547* (2013.01); *A61B 2018/00577* (2013.01); *A61B 2018/00904* (2013.01); *A61B 2018/00982* (2013.01); *A61B 2018/048* (2013.01); *A61B 2034/2048* (2016.02); *A61B 2034/2051* (2016.02); *A61B 2034/2072* (2016.02); *A61B 2218/002* (2013.01); *A61B 2218/007* (2013.01)

(58) Field of Classification Search
    CPC .......... A61B 1/307; A61B 2017/00274; A61B 2034/2072
    See application file for complete search history.

(56) References Cited

U.S. PATENT DOCUMENTS

| | | |
|---|---|---|
| 4,672,963 A | 6/1987 | Barken |
| 4,920,982 A | 5/1990 | Goldstein |
| 4,950,267 A | 8/1990 | Ishihara et al. |
| 4,987,781 A * | 1/1991 | Reimann .............. G01P 15/123 257/417 |
| 5,117,482 A | 5/1992 | Hauber |
| 5,222,185 A | 6/1993 | McCord, Jr. |
| 5,249,585 A | 10/1993 | Turner et al. |
| 5,300,099 A | 4/1994 | Rudie |
| 5,312,399 A | 5/1994 | Hakky et al. |
| 5,330,518 A | 7/1994 | Neilson et al. |
| 5,366,490 A | 11/1994 | Edwards et al. |
| 5,370,609 A | 12/1994 | Drasler et al. |
| 5,370,675 A | 12/1994 | Edwards et al. |
| 5,370,677 A | 12/1994 | Rudie et al. |
| 5,385,544 A | 1/1995 | Edwards et al. |
| 5,409,453 A | 4/1995 | Lundquist et al. |
| 5,413,588 A | 5/1995 | Rudie et al. |
| 5,421,819 A | 6/1995 | Edwards et al. |
| 5,435,805 A | 7/1995 | Edwards et al. |
| 5,464,437 A | 11/1995 | Reid et al. |
| 5,470,308 A | 11/1995 | Edwards et al. |
| 5,470,309 A | 11/1995 | Edwards et al. |
| 5,484,400 A | 1/1996 | Edwards et al. |
| 5,499,998 A | 3/1996 | Meade |
| 5,531,676 A | 7/1996 | Edwards et al. |
| 5,531,696 A | 7/1996 | Edwards et al. |
| 5,531,763 A | 7/1996 | Mastri et al. |
| 5,542,915 A | 8/1996 | Edwards et al. |
| 5,542,916 A | 8/1996 | Hirsch et al. |
| 5,545,171 A | 8/1996 | Sharkey et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,673 A | 9/1996 | Edwards et al. |
| 5,588,960 A | 12/1996 | Edwards et al. |
| 5,591,125 A | 1/1997 | Edwards et al. |
| 5,599,294 A | 2/1997 | Edwards et al. |
| 5,601,591 A | 2/1997 | Edwards et al. |
| 5,628,770 A | 5/1997 | Thome et al. |
| 5,630,794 A | 5/1997 | Lax et al. |
| 5,645,528 A | 7/1997 | Thome |
| 5,667,488 A | 9/1997 | Lundquist et al. |
| 5,672,153 A | 9/1997 | Lax et al. |
| 5,709,680 A | 1/1998 | Yates et al. |
| 5,720,718 A | 2/1998 | Rosen et al. |
| 5,720,719 A | 2/1998 | Edwards et al. |
| 5,776,176 A | 7/1998 | Rudie |
| 5,792,070 A | 8/1998 | Kauphusman et al. |
| 5,797,903 A | 8/1998 | Swanson et al. |
| 5,807,395 A | 9/1998 | Mulier et al. |
| 5,830,179 A | 11/1998 | Mikus et al. |
| 5,843,144 A | 12/1998 | Rudie et al. |
| 5,849,011 A | 12/1998 | Jones et al. |
| 5,861,021 A | 1/1999 | Thome et al. |
| 5,871,481 A | 2/1999 | Kannenberg et al. |
| 5,873,877 A | 2/1999 | McGaffigan et al. |
| 5,880,486 A | 3/1999 | Nakamura et al. |
| 5,897,553 A | 4/1999 | Mulier et al. |
| 5,899,932 A | 5/1999 | Dann et al. |
| 5,938,692 A | 8/1999 | Rudie |
| 5,944,715 A | 8/1999 | Goble et al. |
| 5,951,515 A | 9/1999 | Osterlind |
| 5,957,922 A | 9/1999 | Imran |
| 5,964,752 A | 10/1999 | Stone |
| 5,964,756 A | 10/1999 | McGaffigan et al. |
| 5,976,123 A | 11/1999 | Baumgardner et al. |
| 5,987,360 A | 11/1999 | McGrath et al. |
| 5,990,465 A | 11/1999 | Nakaoka et al. |
| 6,007,571 A | 12/1999 | Neilson et al. |
| 6,009,351 A | 12/1999 | Flachman |
| 6,017,358 A | 1/2000 | Yoon et al. |
| 6,017,361 A | 1/2000 | Mikus et al. |
| 6,036,631 A | 3/2000 | McGrath et al. |
| 6,036,713 A | 3/2000 | Kieturakis |
| 6,053,909 A | 4/2000 | Shadduck |
| 6,063,081 A | 5/2000 | Mulier et al. |
| 6,067,475 A | 5/2000 | Graves et al. |
| 6,077,257 A | 6/2000 | Edwards et al. |
| 6,113,593 A | 9/2000 | Tu et al. |
| 6,122,551 A | 9/2000 | Rudie et al. |
| 6,123,083 A | 9/2000 | McGrath et al. |
| 6,147,336 A | 11/2000 | Oshijima et al. |
| 6,148,236 A | 11/2000 | Dann |
| 6,156,036 A | 12/2000 | Sussman et al. |
| 6,161,049 A | 12/2000 | Rudie et al. |
| 6,179,805 B1 | 1/2001 | Sussman et al. |
| 6,179,836 B1 | 1/2001 | Eggers et al. |
| 6,206,847 B1 | 3/2001 | Edwards et al. |
| 6,210,404 B1 | 4/2001 | Shadduck |
| 6,223,085 B1 | 4/2001 | Dann et al. |
| 6,231,591 B1 | 5/2001 | Desai |
| 6,238,389 B1 | 5/2001 | Paddock et al. |
| 6,238,391 B1 | 5/2001 | Olsen et al. |
| 6,238,393 B1 | 5/2001 | Mulier et al. |
| 6,241,702 B1 | 6/2001 | Lundquist et al. |
| 6,258,087 B1 | 7/2001 | Edwards et al. |
| 6,272,384 B1 | 8/2001 | Simon et al. |
| 6,287,297 B1 | 9/2001 | Woodruff et al. |
| 6,302,903 B1 | 10/2001 | Mulier et al. |
| 6,312,391 B1 | 11/2001 | Ramadhyani et al. |
| 6,315,777 B1 | 11/2001 | Comben |
| 6,348,039 B1 | 2/2002 | Flachman et al. |
| 6,494,902 B2 | 2/2002 | Hoey et al. |
| 6,398,759 B1 | 6/2002 | Sussman et al. |
| 6,409,722 B1 | 6/2002 | Hoey et al. |
| 6,423,027 B1 | 7/2002 | Gonon |
| 6,440,127 B2 | 8/2002 | McGovern et al. |
| 6,461,296 B1 | 10/2002 | Desal |
| 6,471,637 B1 * | 10/2002 | Green ................ A61B 1/00045 600/109 |
| 6,496,737 B2 | 12/2002 | Rudie et al. |
| 6,508,816 B2 | 1/2003 | Shadduck |
| 6,517,534 B1 | 2/2003 | McGovern et al. |
| 6,524,270 B1 | 2/2003 | Bolmsjo et al. |
| 6,537,248 B2 | 3/2003 | Mulier et al. |
| 6,537,272 B2 | 3/2003 | Christopherson et al. |
| 6,544,211 B1 | 4/2003 | Andrew et al. |
| 6,551,300 B1 | 4/2003 | McGaffigan |
| 6,565,561 B1 | 5/2003 | Goble et al. |
| 6,575,929 B2 | 6/2003 | Sussman et al. |
| 6,575,968 B1 | 6/2003 | Eggers et al. |
| 6,579,270 B2 | 6/2003 | Sussman et al. |

(56) References Cited

U.S. PATENT DOCUMENTS

| | | | |
|---|---|---|---|
| 6,589,201 B1 | 7/2003 | Sussman et al. |
| 6,607,529 B1 | 8/2003 | Jones et al. |
| 6,638,275 B1 | 10/2003 | McGaffigan et al. |
| 6,640,139 B1 | 10/2003 | Ueberle |
| 6,669,694 B2 | 12/2003 | Shaddock |
| 6,676,628 B2 | 1/2004 | Sussman et al. |
| 6,706,039 B2 | 3/2004 | Mulier et al. |
| 6,716,252 B2 | 4/2004 | Lazarovitz et al. |
| 6,719,738 B2 | 4/2004 | Mehier |
| 6,726,696 B1 | 4/2004 | Houser et al. |
| 6,730,079 B2 | 5/2004 | Lovewell |
| 6,736,810 B2 | 5/2004 | Hoey et al. |
| 6,740,108 B1 | 5/2004 | Just et al. |
| 6,760,616 B2 | 7/2004 | Hoey et al. |
| 6,780,178 B2 | 8/2004 | Palanker et al. |
| 6,827,718 B2 | 12/2004 | Hutchins et al. |
| 6,855,141 B2 | 2/2005 | Lovewell |
| 6,887,237 B2 | 5/2005 | McGaffigan |
| 6,905,475 B2 | 6/2005 | Hauschild et al. |
| 6,911,028 B2 | 6/2005 | Shadduck |
| 6,969,376 B2 | 11/2005 | Takagi et al. |
| 6,974,455 B2 | 12/2005 | Garabedian et al. |
| 7,014,652 B2 | 3/2006 | Cioanta et al. |
| 7,041,121 B1 | 5/2006 | Williams et al. |
| 7,066,935 B2 | 6/2006 | Swoyer et al. |
| 7,089,064 B2 | 8/2006 | Manker et al. |
| 7,130,697 B2 | 10/2006 | Chomenky et al. |
| 7,238,182 B2 | 7/2007 | Swoyer et al. |
| 7,247,155 B2 | 7/2007 | Hoey et al. |
| 7,261,709 B2 | 8/2007 | Swoyer et al. |
| 7,261,710 B2 | 8/2007 | Elmouelhi et al. |
| 7,322,974 B2 | 1/2008 | Swoyer et al. |
| 7,328,068 B2 | 2/2008 | Spinelli et al. |
| 7,328,069 B2 | 2/2008 | Gerber |
| 7,335,197 B2 | 2/2008 | Sage et al. |
| 7,340,300 B2 | 3/2008 | Christopherson et al. |
| 7,369,894 B2 | 5/2008 | Gerber |
| 7,429,262 B2 | 9/2008 | Woloszko et al. |
| 7,437,194 B2 | 10/2008 | Skwarek et al. |
| 7,470,228 B2 | 12/2008 | Connors et al. |
| 7,549,987 B2 | 6/2009 | Shadduck |
| 7,865,250 B2 | 1/2011 | Mrva et al. |
| 7,894,913 B2 | 2/2011 | Boggs et al. |
| 7,959,577 B2 | 6/2011 | Schmitz et al. |
| 8,048,069 B2 | 11/2011 | Skwarek et al. |
| 8,216,217 B2 | 7/2012 | Sharkey et al. |
| 8,244,327 B2 | 8/2012 | Fichtinger et al. |
| 8,251,985 B2 | 8/2012 | Hoey et al. |
| 8,272,383 B2 | 9/2012 | Hoey et al. |
| 8,273,079 B2 | 9/2012 | Hoey et al. |
| 8,301,264 B2 | 10/2012 | Achenbach et al. |
| 8,313,485 B2 | 11/2012 | Shadduck |
| 8,353,818 B1* | 1/2013 | Sasaki .............. A61B 5/061 |
| | | 396/17 |
| 8,372,065 B2 | 2/2013 | Hoey et al. |
| 8,388,611 B2 | 3/2013 | Shadduck et al. |
| 8,409,109 B2 | 4/2013 | Tiesma et al. |
| 8,419,723 B2 | 4/2013 | Shadduck et al. |
| 8,550,743 B2 | 10/2013 | Bonde et al. |
| 8,585,692 B2 | 11/2013 | Shadduck et al. |
| 8,632,530 B2 | 1/2014 | Hoey et al. |
| 8,740,957 B2 | 6/2014 | Masotti |
| 8,801,702 B2 | 8/2014 | Hoey et al. |
| 8,900,223 B2 | 12/2014 | Shadduck |
| 2001/0047133 A1* | 11/2001 | Gilboa .............. A61B 5/06 |
| | | 600/429 |
| 2002/0078956 A1 | 6/2002 | Sharpe et al. |
| 2002/0111617 A1 | 8/2002 | Cosman et al. |
| 2002/0177846 A1 | 11/2002 | Mulier et al. |
| 2003/0069575 A1 | 4/2003 | Chin et al. |
| 2003/0092689 A1 | 5/2003 | Escandon et al. |
| 2003/0097126 A1 | 5/2003 | Woloszko et al. |
| 2003/0130575 A1 | 7/2003 | Desai |
| 2003/0206730 A1 | 11/2003 | Golan |
| 2004/0006334 A1 | 1/2004 | Beyar et al. |
| 2004/0068306 A1 | 4/2004 | Shadduck |
| 2004/0186422 A1 | 9/2004 | Rioux et al. |
| 2004/0230316 A1 | 11/2004 | Cioanta et al. |
| 2004/0267340 A1 | 12/2004 | Cioanta et al. |
| 2005/0096629 A1 | 5/2005 | Gerber et al. |
| 2005/0124915 A1 | 6/2005 | Eggers et al. |
| 2005/0149020 A1 | 7/2005 | Jahng |
| 2005/0159676 A1 | 7/2005 | Taylor et al. |
| 2006/0079883 A1* | 4/2006 | Elmouelhi ......... A61B 18/1492 |
| | | 606/41 |
| 2006/0089636 A1 | 4/2006 | Christopherson et al. |
| 2006/0135955 A1 | 6/2006 | Shadduck |
| 2006/0178670 A1 | 8/2006 | Woloszko et al. |
| 2006/0224154 A1 | 10/2006 | Shadduck et al. |
| 2006/0224169 A1 | 10/2006 | Weisenburgh, II et al. |
| 2006/0253069 A1 | 11/2006 | Li et al. |
| 2006/0276871 A1 | 12/2006 | Lamson et al. |
| 2007/0003612 A1* | 1/2007 | Williams ................. A61B 5/07 |
| | | 424/451 |
| 2007/0032785 A1 | 2/2007 | Diederich et al. |
| 2007/0038089 A1 | 2/2007 | Hatano et al. |
| 2007/0142846 A1 | 6/2007 | Catanese, III et al. |
| 2007/0179491 A1 | 8/2007 | Kratoska et al. |
| 2007/0197864 A1 | 8/2007 | Dejima et al. |
| 2007/0213703 A1 | 9/2007 | Naam et al. |
| 2008/0021484 A1 | 1/2008 | Catanese, III et al. |
| 2008/0021485 A1 | 1/2008 | Catanese, III et al. |
| 2008/0033232 A1 | 2/2008 | Catanese, III et al. |
| 2008/0033458 A1 | 2/2008 | McLean et al. |
| 2008/0033488 A1 | 2/2008 | Catanese, III et al. |
| 2008/0039833 A1 | 2/2008 | Catanese, III et al. |
| 2008/0039872 A1 | 2/2008 | Catanese, III et al. |
| 2008/0039874 A1 | 2/2008 | Catanese, III et al. |
| 2008/0039875 A1 | 2/2008 | Catanese, III et al. |
| 2008/0039876 A1 | 2/2008 | Catanese, III et al. |
| 2008/0039893 A1 | 2/2008 | McLean et al. |
| 2008/0039894 A1 | 2/2008 | Catanese, III et al. |
| 2008/0046045 A1 | 2/2008 | Yon et al. |
| 2008/0110457 A1 | 5/2008 | Barry et al. |
| 2008/0132826 A1 | 6/2008 | Shadduck et al. |
| 2008/0188811 A1 | 8/2008 | Kim |
| 2008/0208187 A1 | 8/2008 | Bhushan et al. |
| 2008/0214956 A1 | 9/2008 | Briggs et al. |
| 2008/0217325 A1 | 9/2008 | Von Buren et al. |
| 2008/0249399 A1 | 10/2008 | Appling et al. |
| 2008/0262491 A1 | 10/2008 | Swoyer et al. |
| 2008/0269737 A1 | 10/2008 | Elmouelhi et al. |
| 2008/0269862 A1 | 10/2008 | Elmouelhi et al. |
| 2008/0275440 A1 | 11/2008 | Kratoska et al. |
| 2008/0297287 A1 | 12/2008 | Shachar et al. |
| 2008/0312497 A1 | 12/2008 | Elmouelhi et al. |
| 2009/0018553 A1 | 1/2009 | McLean et al. |
| 2009/0054871 A1 | 2/2009 | Sharkey et al. |
| 2009/0138001 A1 | 5/2009 | Barry et al. |
| 2009/0149846 A1 | 6/2009 | Hoey et al. |
| 2009/0199855 A1 | 8/2009 | Davenport |
| 2009/0216220 A1 | 8/2009 | Hoey et al. |
| 2009/0227998 A1 | 9/2009 | Aljuri et al. |
| 2009/0306640 A1 | 12/2009 | Glaze et al. |
| 2010/0016757 A1 | 1/2010 | Greenburg et al. |
| 2010/0049031 A1 | 2/2010 | Fruland et al. |
| 2010/0094270 A1 | 4/2010 | Sharma |
| 2010/0114083 A1 | 5/2010 | Sharma |
| 2010/0179416 A1 | 7/2010 | Hoey et al. |
| 2010/0193568 A1 | 8/2010 | Scheib et al. |
| 2010/0204688 A1 | 8/2010 | Hoey et al. |
| 2010/0256636 A1 | 10/2010 | Fernandez et al. |
| 2010/0262133 A1 | 10/2010 | Hoey et al. |
| 2010/0262137 A1 | 10/2010 | Nye et al. |
| 2010/0286679 A1 | 11/2010 | Hoey et al. |
| 2010/0292767 A1 | 11/2010 | Hoey et al. |
| 2010/0298948 A1 | 11/2010 | Hoey et al. |
| 2011/0060328 A1 | 3/2011 | Skwarek et al. |
| 2011/0077628 A1 | 3/2011 | Hoey et al. |
| 2011/0106072 A1 | 5/2011 | Sundquist et al. |
| 2011/0160648 A1 | 6/2011 | Hoey |
| 2011/0264176 A1 | 10/2011 | Jackson et al. |
| 2011/0319759 A1 | 12/2011 | Liu et al. |
| 2012/0259271 A1 | 10/2012 | Shadduck et al. |

(56) References Cited

U.S. PATENT DOCUMENTS

| | | |
|---|---|---|
| 2012/0265276 A1 | 10/2012 | Curley |
| 2012/0323167 A1 | 12/2012 | Hoey et al. |
| 2013/0006231 A1 | 1/2013 | Sharma et al. |
| 2013/0066308 A1 | 3/2013 | Landman |
| 2013/0072855 A1 | 3/2013 | Sherry et al. |
| 2013/0074847 A1 | 3/2013 | Hoey et al. |
| 2013/0172867 A1 | 7/2013 | Shadduck et al. |
| 2013/0261692 A1 | 10/2013 | Cardinal et al. |
| 2014/0039356 A1 | 2/2014 | Sachs et al. |
| 2014/0107637 A1 | 4/2014 | Hoey et al. |
| 2014/0200568 A1 | 7/2014 | Sharma |
| 2014/0276713 A1 | 9/2014 | Hoey et al. |
| 2014/0288543 A1 | 9/2014 | Hoey et al. |
| 2014/0354381 A1 | 12/2014 | Kohlhafer |
| 2015/0025515 A1 | 1/2015 | Hoey et al. |
| 2015/0025516 A1 | 1/2015 | Hoey et al. |
| 2015/0126990 A1 | 5/2015 | Sharma et al. |
| 2016/0081736 A1 | 3/2016 | Hoey et al. |
| 2017/0056089 A1 | 3/2017 | Hoey et al. |

FOREIGN PATENT DOCUMENTS

| | | |
|---|---|---|
| CN | 101072544 | 11/2007 |
| CN | 101257855 | 9/2008 |
| CN | 101006939 A | 11/2008 |
| CN | 101491458 A | 7/2009 |
| CN | 101803947 A | 8/2010 |
| JP | 7-507696 A | 8/1995 |
| JP | 8-501957 A | 3/1996 |
| JP | 8-504613 A | 5/1996 |
| JP | 11-318925 A | 11/1999 |
| JP | 200014663 A | 1/2000 |
| JP | 2000005191 A | 1/2000 |
| JP | 2001500763 A | 1/2001 |
| JP | 2005137916 A | 6/2005 |
| WO | 92/10142 A1 | 6/1992 |
| WO | 01/24715 A1 | 4/2001 |
| WO | 03/088851 A1 | 10/2003 |
| WO | 03/096871 A2 | 11/2003 |
| WO | 2006004482 A1 | 1/2006 |
| WO | 2008083407 A1 | 7/2008 |
| WO | 2010080467 A2 | 7/2010 |
| WO | 2013160772 A2 | 10/2013 |
| WO | 2015089190 A1 | 6/2015 |

OTHER PUBLICATIONS

Hoey et al.: U.S. Appl. No. 14/773,853 entitled "Systems and methods for treating prostate cancer," filed Sep. 9, 2015.

Hastings et al.: U.S. Appl. No. 15/011,005 entitled "Vapor ablation systems and methods," filed Jan. 29, 2016.

Hastings et al.: U.S. Appl. No. 15/035,944 entitled "Vapor ablation systems and methods," filed May 11, 2016.

Hoey et al.: U.S. Appl. No. 15/154,536 entitled "Systems and methods for treating the bladder with condensable vapor," filed May 13, 2016.

Hai: Photoselective Vaporization Prostatectomy: A Palliative Treatment Option for Men with Urinary Obstruction Secondary to Prostate Cancer; PCRI Prost. Cancer Rsrch. Inst. from PCRI Insights Nov. 2005, vol. 8(4); Dwnld from http://www.prostate-cancer.org/pcricms/node/233 on May 10, 2012; 4 pages.

Nguyen et al.; Updated results of magnetic resonance imaging guided partial prostate brachytherapy for favorable prostate cancer: Implications for focal therapy; J. Urol.; 188(4); pp. 1151-1156; Oct. 2012.

* cited by examiner

SYSTEMS AND METHODS FOR TREATING THE PROSTATE

CROSS REFERENCE TO RELATED APPLICATIONS

This application is a continuation of U.S. application Ser. No. 14/566,448, filed Dec. 10, 2014, now U.S. Pat. No. 9,968,395; which application claims the benefit of U.S. Provisional Patent Application No. 61/914,279, filed Dec. 10, 2013, titled "SYSTEMS AND METHODS FOR TREATING THE PROSTATE", both of which are incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates to devices and related methods for treatment of benign prostatic hyperplasia using a minimally invasive approach.

BACKGROUND

Benign prostatic hyperplasia (BPH) is a common disorder in middle-aged and older men, with prevalence increasing with age. At age 50, more than one-half of men have symptomatic BPH, and by age 70, nearly 90% of men have microscopic evidence of an enlarged prostate. The severity of symptoms also increase with age with 27% of patients in the 60-70 age bracket having moderate-to-severe symptoms, and 37% of patients in their 70's suffering from moderate-to-severe symptoms.

The prostate early in life is the size and shape of a walnut and prior to the enlargement resulting from BPH, weighs about 20 grams. Prostate enlargement appears to be a normal process. With age, the prostate gradually increases in size to twice or more its normal size. The fibromuscular tissue of the outer prostatic capsule restricts expansion after the gland reaches a certain size. Because of such restriction on expansion, the intracapsular tissue will compress against and constrict the prostatic urethra, thus causing resistance to urine flow.

In the male urogenital anatomy, the prostate gland is located below the bladder and the bladder neck. The walls of the bladder can expand and contract to cause urine flow through the urethra, which extends from the bladder, through the prostate and penis. The portion of urethra that is surrounded by the prostate gland is referred to as the prostatic urethra. The prostate also surrounds the ejaculatory ducts which have an open termination in the prostatic urethra. During sexual arousal, sperm is transported from the testes by the ductus deferens to the prostate which provides fluids that combine with sperm to form semen during ejaculation. On each side of the prostate, the ductus deferens and seminal vesicles join to form a single tube called an ejaculatory duct. Thus, each ejaculatory duct carries the seminal vesicle secretions and sperm into the prostatic urethra.

The prostate glandular structure can be classified into three zones: the peripheral zone, transition zone, and central zone. Peripheral zone PZ comprises about 70% of the volume of a young man's prostate. This sub-capsular portion of the posterior aspect of the prostate gland surrounds the distal urethra and 70 to 80% of cancers originate in the peripheral zone tissue. The central zone CZ surrounds the ejaculatory ducts and contains about 20-25% of the prostate volume. The central zone is often the site of inflammatory processes. The transition zone TZ is the site in which benign prostatic hyperplasia develops, and contains about 5-10% of the volume of glandular elements in a normal prostate, but can constitute up to 80% of such volume in cases of BPH. The transition zone consists of two lateral prostate lobes and the periurethral gland region. There are natural barriers around the transition zone, i.e., the prostatic urethra, the anterior fibromuscular stroma, and a fibrous plane between the transition zone and peripheral zone. The anterior fibromuscular stroma or fibromuscular zone is predominantly fibromuscular tissue.

BPH is typically diagnosed when the patient seeks medical treatment complaining of bothersome urinary difficulties. The predominant symptoms of BPH are an increase in frequency and urgency of urination, and a significant decrease in the rate of flow during urination. BPH can also cause urinary retention in the bladder which in turn can lead to lower urinary tract infection (LUTI). In many cases, the LUTI then can ascend into the kidneys and cause chronic pyelonephritis, and can eventually lead to renal insufficiency. BPH also may lead to sexual dysfunction related to sleep disturbance or psychological anxiety caused by severe urinary difficulties. Thus, BPH can significantly alter the quality of life with aging of the male population.

BPH is the result of an imbalance between the continuous production and natural death (apoptosis) of the glandular cells of the prostate. The overproduction of such cells leads to increased prostate size, most significantly in the transition zone which traverses the prostatic urethra.

In early stage cases of BPH, pharmacological treatments can alleviate some of the symptoms. For example, alpha-blockers treat BPH by relaxing smooth muscle tissue found in the prostate and the bladder neck, which may allow urine to flow out of the bladder more easily. Such drugs can prove effective until the glandular elements cause overwhelming cell growth in the prostate.

More advanced stages of BPH, however, can only be treated by surgical or less-invasive thermal ablation device interventions. A number of methods have been developed using electrosurgical or mechanical extraction of tissue, and thermal ablation or cryoablation of intracapsular prostatic tissue. In many cases, such interventions provide only transient relief, and these treatments often cause significant peri-operative discomfort and morbidity.

In one thermal ablation method, RF energy is delivered to prostate tissue via an elongated RF needle being penetrated into a plurality of locations in a prostate lobe. The elongated RF needle is typically about 20 mm in length, together with an insulator that penetrates into the lobe. The resulting RF treatment thus ablates tissue away from the prostatic urethra and does not target tissue close to, and parallel to, the prostatic urethra. The application of RF energy typically extends for 1 to 3 minutes or longer which allows thermal diffusion of the RF energy to ablate tissue out to the capsule periphery. Such RF energy delivery methods may not create a durable effect, since smooth muscle tissue and alpha adrenergic receptors are not uniformly ablated around the prostatic urethra or within the transition zone. As a result, tissue in the prostate lobes can continue to grow and impinge on the urethra thus limiting long-term effectiveness of the treatment.

SUMMARY OF THE DISCLOSURE

A method for treating a prostate is provided, comprising the steps of inserting a vapor delivery system into a urethra of a patient, advancing a distal portion of the vapor delivery system to a bladder neck of the patient, viewing the distal portion of the vapor delivery system with a camera disposed on or within the vapor delivery system, measuring a distance from the bladder neck to a first treatment region in a first lobe of the prostate with a field of view of the camera, pulling the distal portion of the vapor delivery system proximally across the field of view of the camera to the first treatment region, deploying a vapor delivery needle from the vapor delivery system into the first treatment region of the first lobe, and delivering vapor into the first treatment region of the first lobe of the prostate to ablate tissue in the prostate.

In one embodiment, the method further comprises, prior to the measuring step, measuring a distance from the bladder neck to a veru of the patient.

In another embodiment, the method further comprises determining a number of treatments to perform based on the distance from the bladder neck to the veru.

In some embodiments, the delivering step comprises delivering between 160-300 calories of energy into the prostate.

In another embodiment, the measuring step further comprises determining a distance traveled by the vapor delivery system when it is moved across the field of view of the camera.

In one embodiment, the method further comprises measuring a distance from the first treatment region in the prostate to a second treatment region in the prostate with the field of view of the camera, pulling the distal portion of the vapor delivery system proximally across the field of view of the camera to the second treatment region, deploying a vapor delivery needle from the vapor delivery system into the second treatment region of the prostate, and delivering vapor into the second treatment region of the prostate to ablate tissue in the prostate.

In some embodiments, the second treatment region overlaps with the first treatment region.

In one embodiment, a center of the first treatment region is approximately 1 cm apart from a center of the second treatment region.

In one embodiment, the method further comprises measuring a distance from the second treatment region in the prostate to a third treatment region in the prostate with the field of view of the camera, pulling the distal portion of the vapor delivery system proximally across the field of view of the camera to the third treatment region, deploying a vapor delivery needle from the vapor delivery system into the third treatment region of the prostate, and delivering vapor into the third treatment region of the prostate to ablate tissue in the prostate.

In some embodiments, the third treatment region overlaps with the second treatment region.

In one embodiment, the method further comprises repeating the measuring, pulling, deploying, and delivering steps for a second lobe of the prostate.

In some embodiments, the field of view of the camera spans a distance of approximately 0.5 cm.

In another embodiment, the measuring step further comprises identifying an anatomical landmark near a proximal portion of the field of view of the camera, and wherein the pulling step further comprises pulling the distal portion of the vapor delivery system proximally across the field of view of the camera until the anatomical landmark is positioned near a distal portion of the field of view of the camera.

In one embodiment, the method further comprises automatically tracking the anatomical landmark with a digital image processing software running on an electronic controller of the vapor delivery system.

In another embodiment, the method further comprises sensing an orientation of the vapor delivery needle with a sensor of the vapor delivery system.

In one embodiment, the sensor comprises an accelerometer. In another embodiment, the sensor comprises a gyroscope.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

DETAILED DESCRIPTION OF THE INVENTION

In general, one method for treating BPH comprises introducing a heated vapor interstitially into the interior of a prostate, wherein the vapor controllably ablates prostate tissue. This method can utilize vapor for applied thermal energy of between 50 calories and 300 calories per each individual vapor treatment (and assumes multiple treatments for each prostate lobe) in an office-based procedure. The method can cause localized ablation of prostate tissue, and more particularly the applied thermal energy from vapor can be localized to ablate tissue adjacent the urethra without damaging prostate tissue that is not adjacent the urethra.

The present disclosure is directed to the treatment of BPH, and more particularly for transurethrally ablating transitional zone prostate tissue without ablating central or peripheral zone prostate tissue or the urethra. In one embodiment, the present disclosure is directed to treating a prostate using convective heating in a region adjacent the prostatic urethra. The method of ablative treatment is configured to target smooth muscle tissue, alpha adrenergic receptors, sympathetic nerve structures and vasculature parallel to the prostatic urethra between the bladder neck region and the verumontanum region to a depth of less than 2 cm.

The system can include a vapor delivery mechanism that delivers vapor media, including water vapor. The system can utilize a vapor source configured to provide vapor having a temperature of at least 60-140° C. In another embodiment, the system further comprises a computer controller configured to deliver vapor for an interval ranging from 1 second to 30 seconds.

In some embodiments, the system further comprises a source of a pharmacologic agent or other chemical agent or compound for delivery with the vapor. These agents include, without limitation, an anesthetic, an antibiotic or a toxin such as Botox®, or a chemical agent that can treat cancerous tissue cells. The agent also can be a sealant, an adhesive, a glue, a superglue, an anti-inflammatory, an antibiotic, or the like.

Figure 1:
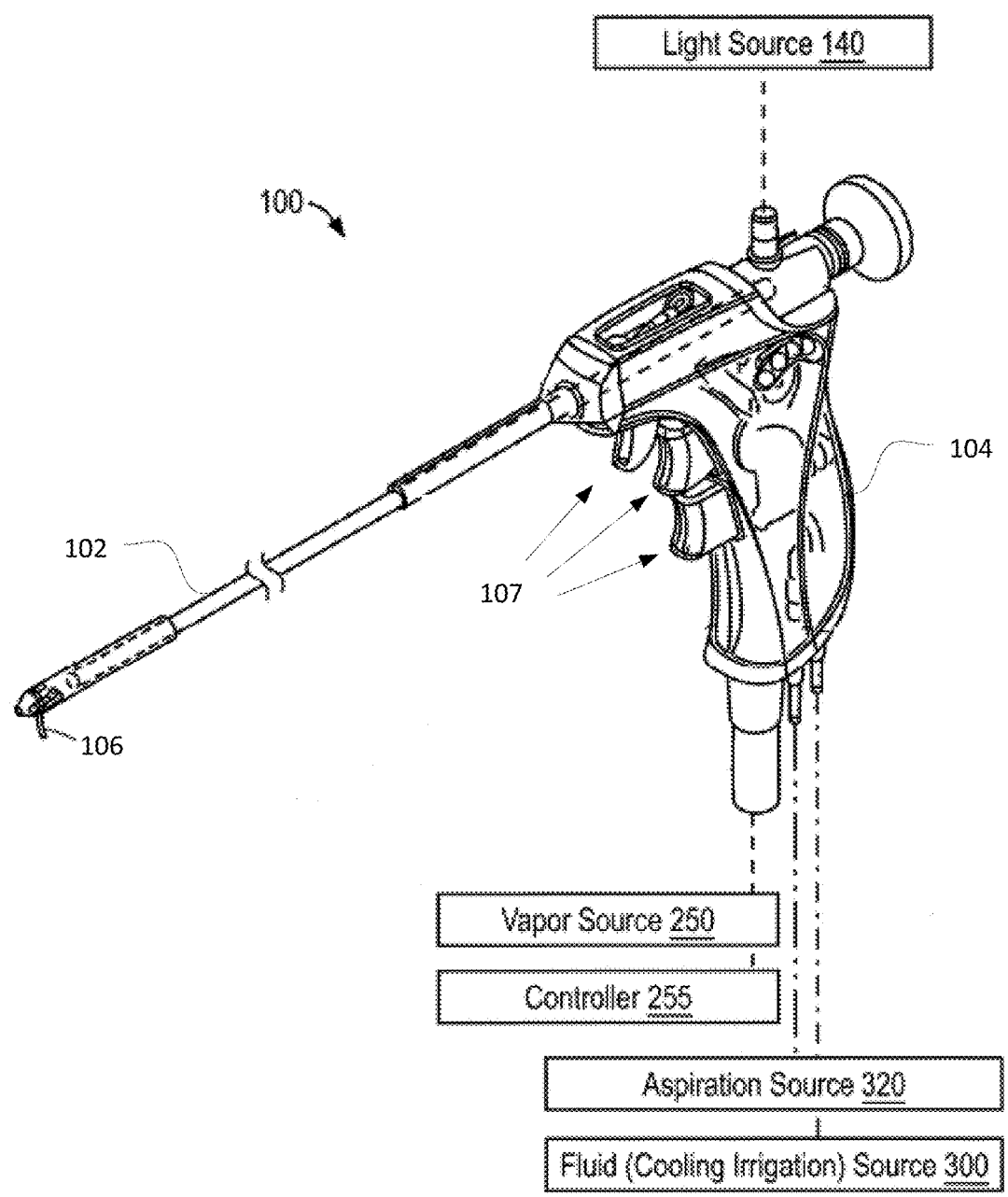
FIG. 1 shows one embodiment of a vapor delivery system.

FIG. 1 shows one embodiment of a vapor delivery system. Vapor delivery system 100 can have an elongate shaft 102 configured for insertion into the urethra of a patient and a handle portion 104 for gripping with a human hand. The vapor system 100 can include a vapor delivery needle 106 configured to extend from a distal portion of the elongate shaft 102. In some embodiments, the vapor delivery needle 106 can be retracted within the shaft during insertion of the shaft into the urethra of the patient, and the vapor delivery needle can then be advanced from the shaft into the prostate tissue when the system is properly placed within the patient. In one embodiment, the vapor delivery needle extends outwards in a generally perpendicular direction to the elongate shaft. The vapor delivery needle can extend generally perpendicular to or transverse from the shaft, and can include one or more vapor delivery ports configured to deliver a flow of vapor media from a vapor source 250 through the vapor delivery needle 106 into prostate tissue. The vapor delivery needle can further include an aspiration source 320 configured to aspirate tissue and/or fluids from the patient (e.g., either through the vapor delivery ports or through separate aspiration ports in the vapor delivery needle), and can also include a fluid source 300 configured to deliver a fluid or cooling irrigation to the tissue before, during, and/or after vapor delivery.

The vapor delivery system 100 of FIG. 1 can include a plurality of actuation mechanisms 107, such as triggers, buttons, or levers, configured to actuate the various functions of the system. For example, the actuation mechanism can be configured to extend/retract the vapor delivery needle, and start/stop the flow of vapor, aspiration, and/or the cooling irrigation.

Vapor source 250 is provided for delivering a vapor media through the vapor delivery needle to ablate tissue. The vapor source can be a vapor generator that can deliver a vapor media, such as water vapor, that has a precisely controlled quality to provide a precise amount of thermal energy delivery, for example measured in calories per second. In some embodiments, the vapor source can comprise an inductive heating system similar in which a flow media is inductively heated to generate a condensable vapor. The controller 255 can be set to control the various parameters of vapor delivery, for example, the controller can be set to delivery vapor media for a selected treatment interval, a selected pressure, or selected vapor quality. Further details on the vapor delivery system, the vapor generator, and how vapor and fluid are delivered to tissue can be found in U.S. Pat. No. 8,273,079 and PCT Publication No. WO 2013/040209, both of which are incorporated by reference. In some embodiments, the electronic controller can also control the aspiration and/or cooling irrigation functions of the vapor delivery system.

Figure 2:
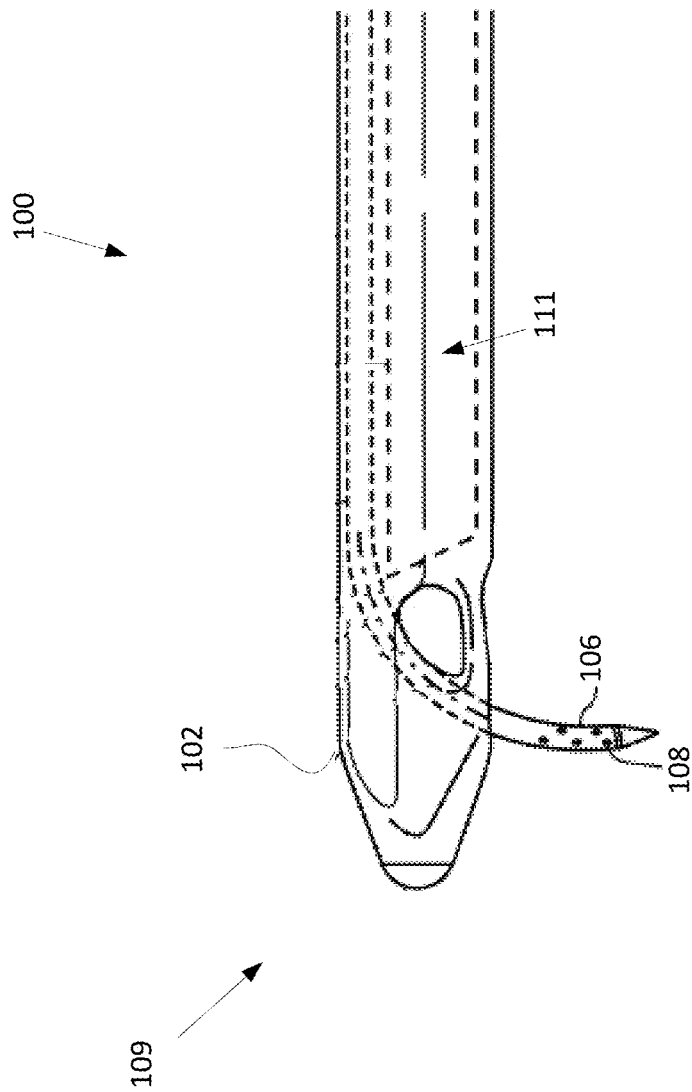
FIG. 2 shows a close-up view of a distal portion of the vapor delivery system.

FIG. 2 shows a close-up view of a distal portion 109 of the elongate shaft of vapor delivery system 100, including the vapor delivery needle 106 extending beyond the shaft and exposing the vapor delivery ports 108. The vapor delivery system 100 can further include one or more lumens 111 sized to accommodate an endoscope or camera to provide additional viewing and feedback to the physician during use. This endoscope or camera can provide a view of the distal portion of the shaft, including a view of the vapor delivery needle when deployed and inserted into tissue.

As described above, the vapor delivery system can be connected to a vapor source 250, an aspiration source 320, a fluid or irrigation source 300, a light source 140, and an electronic controller 255 configured to control generation and delivery of vapor from the vapor source, through a lumen of the shaft, through the vapor delivery needle, and into tissue. In some embodiments, the electronic controller can be disposed on or in the vapor delivery system, and in other embodiments the electronic controller can be disposed separate from the system.

Referring still to FIG. 1, the fluid or irrigation source 300 can provide a fluid, such as saline, through a separate lumen in the shaft to provide irrigation and flushing to tissue during insertion of the system and during vapor delivery to tissue. In some embodiments, the irrigation can be used to clear blood and debris from tissue lumens to increase visibility. The irrigation can also provide cooling to the urethra of the patient, both via direct contact of the irrigation fluid with the urethra as well as cooling the shaft of the vapor delivery system as the fluid flows from the irrigation source through the shaft and into contact with the tissue. Urethral flush can be used during the vapor delivery and lesion formation. In one embodiment, the flush rate can be approximately 80 mL/minute, or ranging from 20 to 400 mL/minute. Changes in flush rate will change the amount of tissue cooling (depth) into the urethra and prostate, which can affect lesion size.

Figure 3:
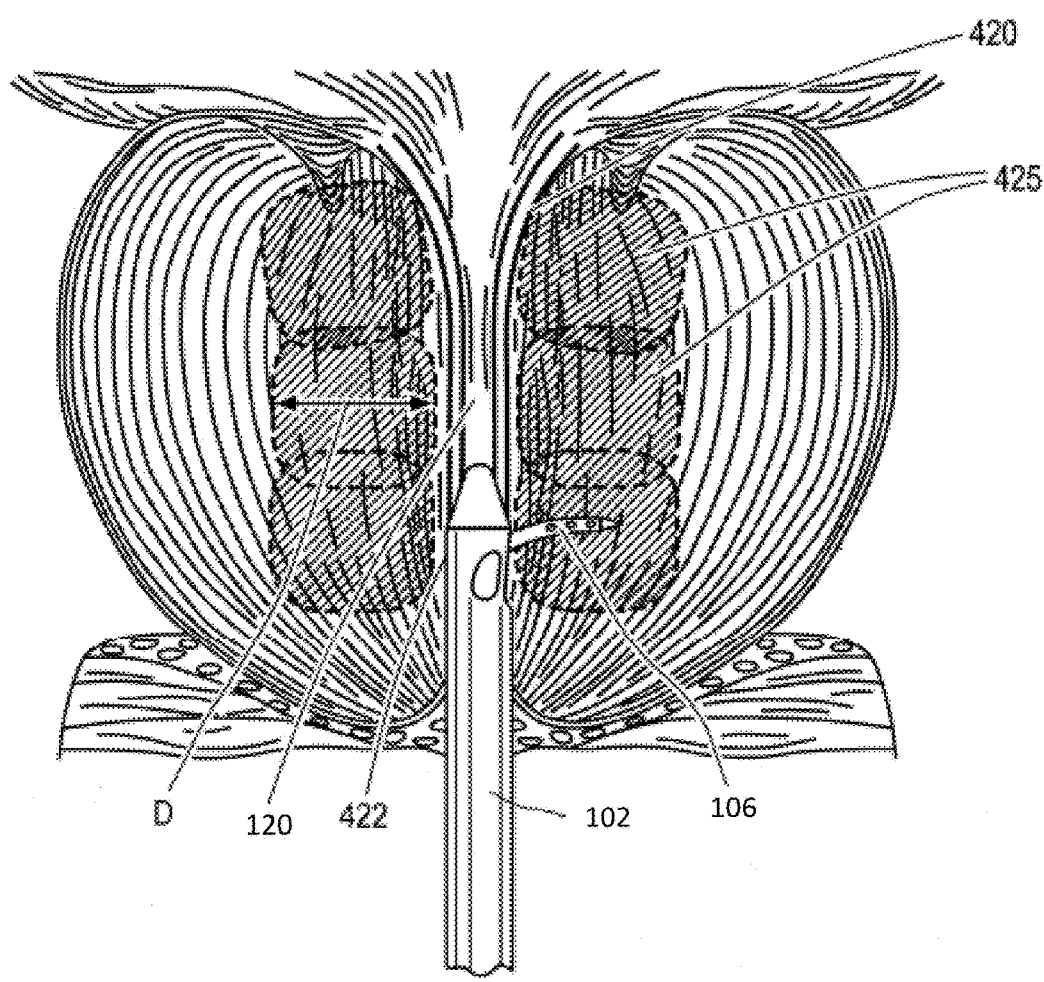
FIG. 3 shows one method of treating a prostate with the vapor delivery system.

Referring to FIG. 3, the device and method of this disclosure provide a precise, controlled thermal ablative treatment of tissue in the first and second lateral prostate lobes (or right- and left-side lobes), and additionally an affected median lobe in patients with an enlarged median lobe. In particular, the ablative treatment is configured to ablate stromal or smooth muscle tissue, to ablate alpha adrenergic (muscle constriction) receptors, to ablate sympathetic nerve structures, and to ablate vasculature in the treatment zone.

More in particular, the method of ablative treatment shown in FIG. 3 targets smooth muscle tissue, alpha adrenergic receptors, sympathetic nerve structures, and vasculature parallel to the prostatic urethra between the bladder neck region 420 and the verumontanum region 422. The elongate shaft 102 of the system is configured to access the prostate transurethrally, and vapor delivery needle 106 can be extended generally transverse to the shaft through the urethra to access the prostate, as shown. The targeted ablation regions 425 have a depth indicated at D that is less than 2 cm from the prostatic urethra 120, or less than 1.5 cm. Depending on the length of the patient's prostatic urethra 120, the number of ablative energy deliveries can range from 1 to 4 and typically is 2 or 3. As shown in FIG. 3, vapor treatment can target 1-4 optionally overlapping lesions within each lobe of the prostate arranged close to the prostatic urethra. The lesions can be approximately 1-5 cm$^3$ in size according to one embodiment.

According to one embodiment, the intent of the vapor treatment is to apply vapor to the tissue in the transition zone on each side of the urethra so that the hyperplastic diseased tissue can be absorbed and the urethra is then opened up for voiding. The transition zone has no function in the prostate and is hyperplastic diseased tissue that gets in the way of the prostate's normal function, which is to provide secretions. It also gets in the way of urine flow by creating an obstruction causing resistance in the urethra. According to one embodiment, vapor can be delivered to the transition zone to allow the tissue to shrink and thereby relieve the obstruction.

Referring to FIG. 3, the transition zone starts a couple millimeters proximal from the bladder neck 420 and extends to a couple of millimeters distal from the veru 422, relative to the shaft of the vapor delivery system inserted into the patient.

During a vapor delivery procedure, it is important for the physician to understand the anatomy on the other side of the urethra, and to visualize the hyperplastic tissue. Visualization and understanding placement within the urethra can be challenging during a transurethral procedure. In one embodiment, the field of view (FOV) of an endoscope or camera disposed on or within the vapor delivery system can be utilized to determine positioning of the vapor delivery needle within the patient. In one specific embodiment, the physician can utilize the bladder neck 420 and veru 422 as treatment landmarks during positioning of the vapor delivery needle.

It is important not to advance the needle distally from the bladder neck (with reference to the vapor delivery system), or proximally from the veru (with reference to the vapor delivery system), because inserting a needle into the prostate at those locations in the anatomy risks treating undesired locations, such as the bladder, or puncturing through the prostate capsule and missing the transition zone. Needle deployment regions are typically recommended at least 1 cm proximally from the bladder neck and distally from the veru, with reference to the vapor delivery system, to avoid puncturing through the prostate capsule or the bladder.

In some embodiments, the median lobe can be treated in the same way as the transition zone because it doesn't provide any function. The median lobe is a hyperplastic growth extending from the central zone of the prostate. This tissue can obstruct the flow of urine. In one embodiment, the vapor delivery needle can be distended into the median lobe at an angle to prevent the possibility of the needle puncturing the rectum. Overlapping 1.-5 cm$^3$ lesions can be created in the median lobe just like in the transition zone above. Typically the needle can be inserted into the tissue laterally at a 45 degree angle.

The amount of energy deposited into the prostate tissue is dependent upon the amount of vapor energy coming out of our device and the amount of heat that is drawn away by the flush or irrigation in the urethra. Therefore, the amount of irrigation fluid delivered and vapor energy deposited can be balanced to protect the urethra while allowing for ablation of the prostate tissue. As described above, the irrigation flush is also essential for visualization.

FIGS. 4A-4D illustrate one embodiment of a method of delivering vapor transurethrally into the prostate. Prior to a procedure, a physician can review pre-treatment imaging such as transrectal ultrasound, MRI, CT scan, cystoscopy, etc., to determine the dimensions of the prostate to estimate the number of vapor treatments needed. In one embodiment, a prostate having a length less than 2.5 cm would be given one treatment (1.5-2 cm lesion) per lobe, a prostate having a length from 2.5-4 cm would be given two treatment (1.5-2 cm lesions) per lobe, and a prostate having a length greater than 4 cm would be given three treatments (1.5-2 cm lesions) per lobe.

Figure 4A:
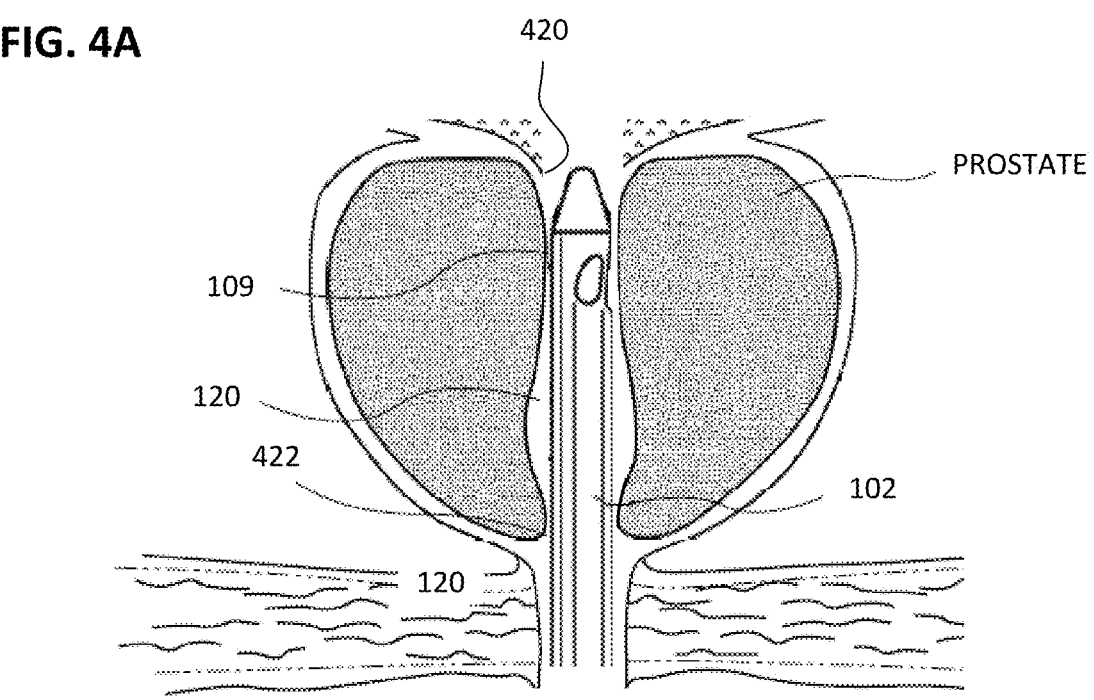
FIGS. 4A, 4B, 4C, 4D and 4E show another method of treating a prostate with the vapor delivery system.

Referring to FIG. 4A, the elongate shaft 102 of the vapor delivery system can be inserted transurethrally into the patient to gain access to the prostatic urethra 120. The physician can identify the veru 422 and surroundings (i.e., prostate height, veru length, lateral tissue bulk, lateral opening) via a camera or endoscope disposed within the elongate shaft, and can advance the distal portion 109 of the shaft towards bladder neck 420 and note surroundings (median lobe, bladder PVR, steepness to get to bladder neck, lateral tissue bulk, ceiling). If an elevated bladder neck is present, the physician can rotate the device to 3 or 9 o'clock and proceed towards the bladder neck. In some instances, the patient anatomy may restrict the device from reaching the bladder neck. In these instances, vapor delivery proximal to the bladder neck may relax the urethra to allow the device to reach the bladder neck.

Figure 4B:
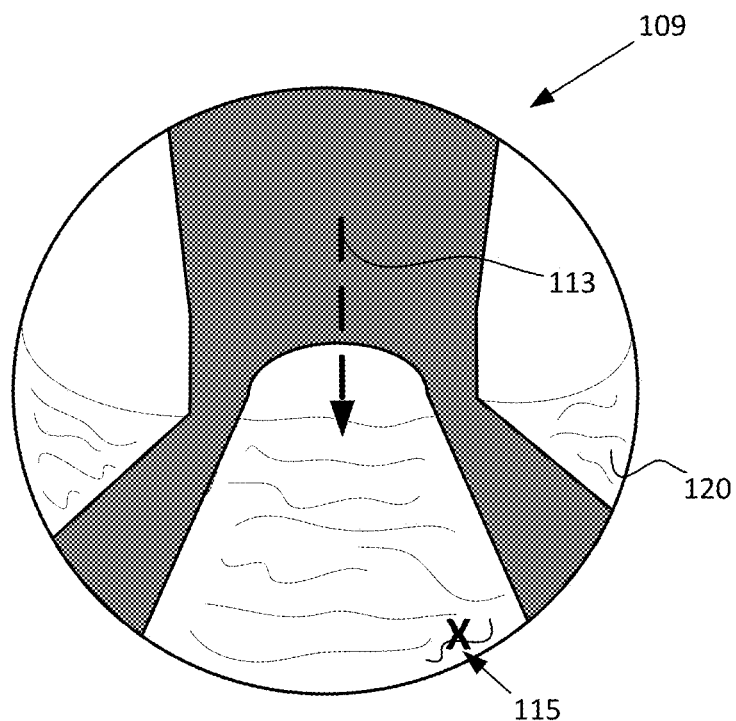
Figure 4C:
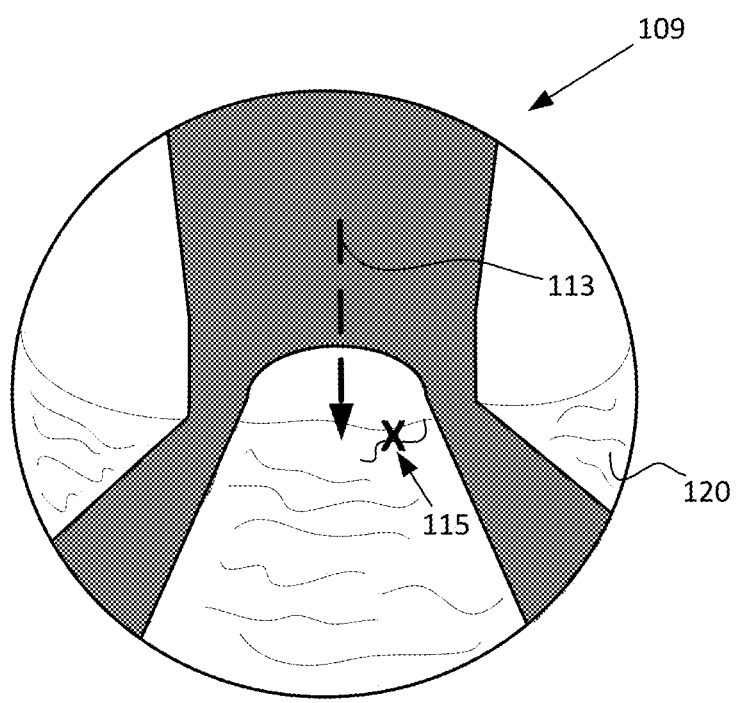

FIG. 4B shows a perspective view of the distal portion 109 of the vapor delivery system, as the system is inserted into the prostatic urethra 120 of the patient. The view shown in FIG. 4B is similar to the view that a physician would see through a camera or endoscope when the vapor delivery system is inside the prostatic urethra. Referring to FIG. 4B, once the distal portion 109 of the vapor delivery system has reached the bladder neck 420, the physician can position the vapor delivery system at a 6 o'clock position. Next, the physician can measure the distance from the bladder neck 420 to the veru using the field of view of the camera or endoscope as a measuring device. Using this technique, the field of view of the camera or endoscope must be known. Typically, each field of view of a standard endoscopic camera is approximately 0.5 cm. It should be understood that with other focal lengths of cameras, the distance per FOV may change but the FOV can still be used to accurately measure distance within the patient. Under visualization, the physician can identify an anatomical landmark 115 near the proximal portion (bottom) of the FOV of the camera. The anatomical landmark can be, for example, a wrinkle or fold in the tissue, a blood vessel, a mark, injury, or other visible landmark in the tissue. In FIG. 4B, the anatomical landmark 115 is a wrinkle or fold in the prostatic urethra 120. The physician can then pull back (proximally) on the elongate shaft of the vapor delivery system until that anatomical landmark is near the distal portion (top) end of the FOV of the camera, as shown in FIG. 4C. Using this technique, the physician can know how far the shaft has been moved within the patient (in this instance, each FOV of movement corresponds to approximately 0.5 cm of movement). Using this measurement technique, the physician can measure the distance from the bladder neck to the veru to confirm or modify pre-treatment plan based on current rigid cysto view measurements. This measurement technique (shown in FIGS. 4B-4C) can be repeated until the physician observes the veru in the FOV of the camera or endoscope.

Figure 4D:
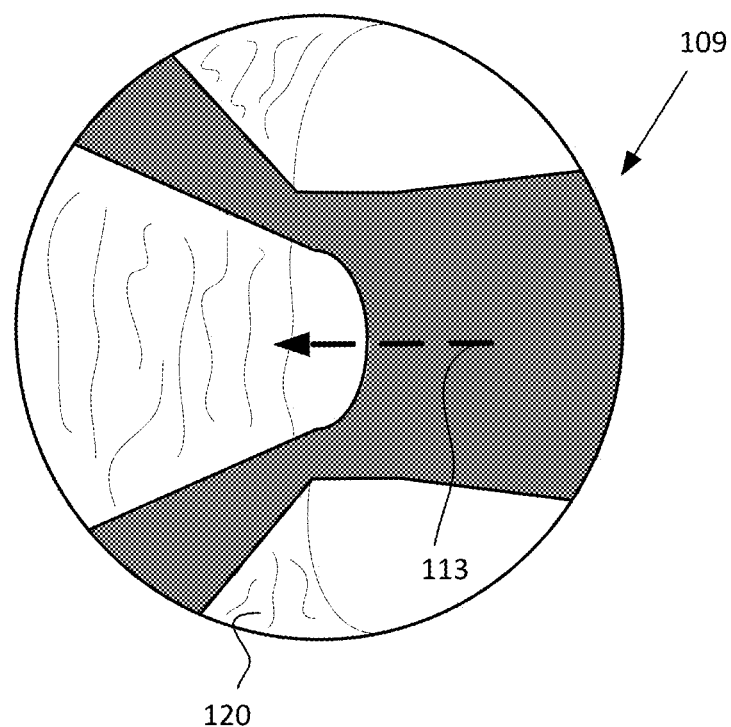
Figure 4E:
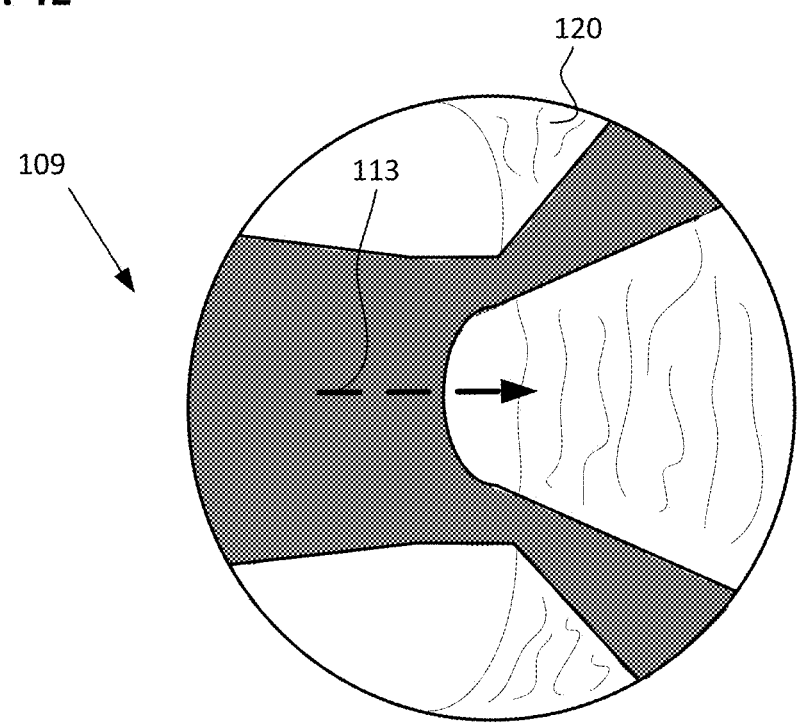

Next, at FIG. 4D, the physician can once again advance the distal end of the shaft back to the bladder neck of the patient. The physician can then rotate the vapor delivery system approximately 90 degrees (either to 3 o'clock or 9 o'clock) at the bladder neck, ensuring measurements begin where actual prostate begins. In FIG. 4D, the vapor delivery system is shown rotated 90 degrees so that the vapor delivery needle would deploy in the 9 o'clock position into the tissue as shown by arrow 113 (and thus into the left lobe of the prostate), and FIG. 4E shows the vapor delivery system rotated 90 degrees into the 3 o'clock position.

The physician can be instructed not to measure from the floor of urethra or the "diving board" into the bladder, but to measure laterally to ensure proper visualization of whole prostate tissue. In one embodiment, the physician can measure approximately 1 cm (e.g., 1-2 FOV's) proximally from the bladder neck 420 and deploy the vapor delivery needle to deliver vapor into the prostate tissue. This first needle deployment can correspond to one of the top lesions shown in FIG. 3 near the bladder neck 420. In some embodiments, the vapor can be delivered for up to approximately 10 seconds or less to create the desired lesion in tissue. Although the lesion is positioned approximately 1 cm from the bladder neck, the lesion will expand to provide ablation coverage up to the bladder neck. The vapor delivery needle can be held in place for a few seconds after the vapor delivery to prevent vapor from escaping into the urethra of the patient.

After the first lesion is formed in the tissue, the physician can continue to form lesions every~1 cm (1-2 FOV's) along the prostate according to the treatment plan above, until the desired number of treatments is reached. Referring to FIG. 3, it is desirable to form contiguous, overlapping lesions in both lobes of the prostate. As a safety precaution prior to deploying the vapor delivery needle, the device can be held at 90 degrees and dipped down for a veru check ensuring the device is distal to the veru (towards the bladder from the veru).

FIG. 4D shows the vapor delivery system positioned at approximately 9 o'clock, for treatment of the left prostate lobe. At FIG. 4E, the physician can advance the device back to the bladder neck and position the vapor delivery system at approximately 3 o'clock to treat the other prostate lobe according to the same procedures outlined above.

On average, peripheral zones comprise about 10 grams of the overall prostate mass. The transition zone is growing while the peripheral zone is not. As such the relative percentage of transition zone tissue to peripheral zone tissue increases over time. The typical patient population for this procedure has a high percentage of transition zone tissue since they are experiencing BPH symptoms. Having said that, prostate measurements can be used as a guide to determine how many calories or vapor injections a given prostate volume merits.

According to one embodiment, a therapy objective includes providing a safe, efficacious, minimally invasive therapy that results in shrinking the transition zone tissue while maintaining low catheterization duration post procedure and minimal medication peri-procedure.

A contiguous lesion from the bladder neck to the verumontanum in each lobe of the prostate (9 o'clock and 3 o'clock positions) is desired. Patients with median lobes also may require treatment of the median lobe. It is desirable to avoid damage to the bladder neck which can create short term irritative symptoms, and treating beyond the verumontanum can result in the vapor going outside the prostate.

It is important that the physician maintain knowledge of the orientation of the vapor delivery needle relative to the patient anatomy so as to prevent accidental delivery of vapor downward toward the rectum. Prostate to rectum fistulas can be dangerous and even life threatening of gone undetected. In some embodiments, one or more sensors may be placed on or in the vapor delivery system to sense a position and/or orientation of the needle. The sensor can provide information to the electronic controller to alert the operator if the needle points, for example, more than 45 degrees down from horizontal. In some embodiments, the sensor(s) can comprise an accelerometer or a gyroscope, for example.

In one specific embodiment, lesions are created using 200-220 calories of vapor, or optionally 160-300 calories of vapor.

In some embodiments, the method of using the field of view of a video image disclosed herein may be automated by using digital image processing software running in the electronic controller of the vapor delivery system to identify and track features that are selected by the user or by the software.

In some embodiments, automated catheter localization may be employed to aid the physician in determining optimal lesion location. In one specific embodiment, GPS systems may broadcast AC magnetic fields from antennas located around the patient. Sensors located on the vapor delivery system can then receive the signals from the antenna array and process the signals to determine the location and orientation of the sensors on the vapor delivery system. In another example, inertial navigation chips that include sensors and a microprocessor may be used to track the location and orientation of a medical device.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A method for treating a prostate, comprising the steps of:
   inserting a shaft of a vapor delivery system into a urethra of a patient;
   advancing a distal portion of the shaft toward a bladder neck of the patient;
   determining a first position of the shaft using at least one sensor disposed on the shaft;
   moving the distal portion of the shaft towards a veru;
   during the moving step, determining a second position of the shaft using the at least one sensor;
   deploying a vapor delivery needle from the shaft into a first treatment region of the prostate; and
   delivering vapor via the vapor delivery needle into the first treatment region of the prostate to ablate tissue in the prostate, wherein the moving step occurs prior to delivery of any vapor to the prostate via the vapor delivery needle
   wherein the determining the first position, the moving, the determining the second position, the deploying, and the delivering steps are performed for a first lobe of the prostate of the patient, the method further comprising;
   repeating the determining the first position, the moving, the determining the second position, the deploying, and the delivering steps for a second lobe in the prostate of the patient.

2. The method of claim 1, further comprising:
   using the determined second position of the shaft, measuring a distance from the bladder neck to the veru of the patient.

3. The method of claim 2, further comprising:
   determining a number of treatments to perform based on the measured distance from the bladder neck to the veru.

4. The method of claim 1, wherein the delivering step comprises delivering between 160-300 calories of energy into the prostate.

5. The method of claim 1, wherein the determining the second position of the shaft includes determining an orientation of the shaft.

6. The method of claim 1, wherein the at least one sensor includes at least one of an accelerometer, an inertial navigation chip, a gyroscope, or a GPS sensor.

7. The method of claim 1, further comprising a plurality of emitters located around the patient, wherein the determining the first position step comprises:
- broadcasting AC magnetic fields via the plurality of emitters;
- receiving the AC magnetic fields via the at least one sensor;
- processing the received AC magnetic fields with the at least one sensor to determine the location and orientation of the at least one sensor.

* * * * *